Dec. 23, 1958 M. W. FISHER Plant Pat. 1,781
GLADIOLUS PLANT
Filed Jan. 17, 1958
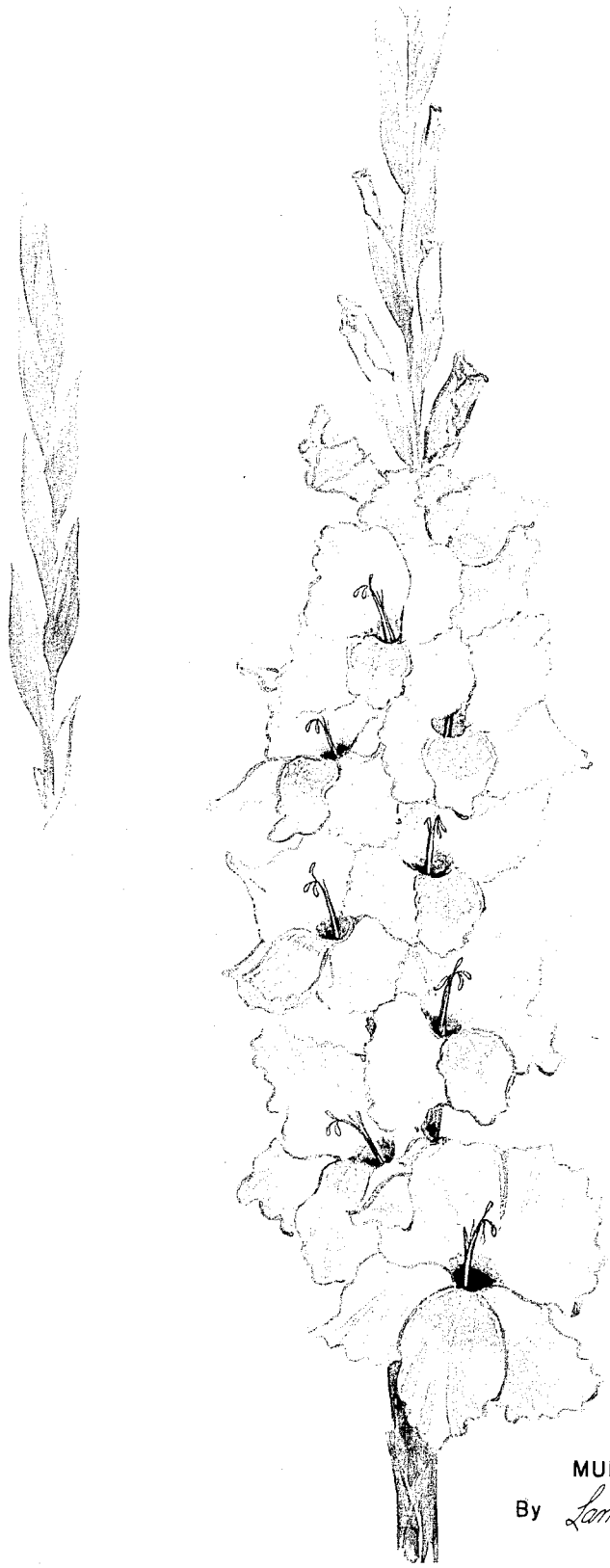
INVENTOR
MURRAY W. FISHER
By Lamont Johnston
ATTORNEY United States Patent Office Plant Pat. 1,781
Patented Dec. 23, 1958

1,781

GLADIOLUS PLANT

Murray W. Fisher, Burlington, Ontario, Canada, assignor to Selected Glads, Inc., Nashville, Tenn., a corporation of Tennessee Application January 17, 1958, Serial No. 709,713

1 Claim. (Cl. 47—60)

My present invention relates to a new and improved variety of gladiolus and is notable particularly for its size, unusual color blend and distinctiveness. I have identified this new variety as seedling No. 7–101–02 in my breeding work.

To the best of my knowledge, this new variety is the result of a cross between the varieties Ogarita (unpatented) and Burma (unpatented). Ogarita is the seed parent and Burma is the pollen parent. Hand cross pollination was done by me in my field at Burlington, Ontario, Canada, but no precaution was taken to prevent admixture of other varieties by bees or insects.

This new variety has been asexually reproduced in my field at Burlington, Ontario, Canada, by natural increase from cormels through several generations and its characteristics have proved to be permanently fixed.

The illustration, made a part of this application, shows two views of a single bloom spike of this new variety and is as nearly true to color as it is possible to depict. The view to the right shows the lower part of the spike and the view to the left shows the upper part. The illustration shows the shape and symmetry of the spike as well as the unusual coloring and the distinctive marking. The illustration is, of course, greatly reduced.

In the following detailed description, color plate references are to the "Horticultural Colour Chart," by The British Colour Council. Where there are other references to color, the ordinary dictionary meanings of the terms are intended.

*The plant*

Growth: Very vigorous. Tall, usually attaining a height of 65 inches. Propagation is moderate.

Blooming: Each spike generally has a total of 20 to 24 buds and flowers with 6 to 9 florets being open at once. This variety will bloom in about 85 days from date planted, from large bulbs.

Foliage: Deep green. Usually large plant. Six or seven leaves. Upright; 24 to 30 inches high. Average leaf is 2 inches wide.

Stems: Usually straight. Diameter at base is from ½ to ¾ inches.

Disease resistance: This variety has been found resistant to Sclerotina Dry Rot, Septoria Leaf Spot and Fusarium Yellows to which other varieties in my field have been subject, observed when grown as a seedling in the sandy loam in the vicinity of Burlington, Ontario, Canada, under the natural conditions provided by the climate of that area. At the end of the season, it would be found that many other varieties and seedlings had succumbed or been badly affected by the various diseases, whereas this variety remained healthy and unaffected.

Corms: This variety produces large, very smooth bulbs. The husks are tinted red to a medium red. The flesh of the bulbs comes closest to Brick Red 016 in color.

*The flower*

Spike: Long, has 20–24 buds of which 3 or 4 open the first day; following which 7 to 9 are open the second day.

Bud:

*Size.*—Opening buds are 2½ to 3¼ inches long.

*Opening.*—5 or 6 will show color at one time, 3 to 4 opening the first day.

Flower:

*Arrangement.*—Flowers are placed in double row on the stem and usually all face forward.

*Size.*—Individual florets are exceptionally large, usually measuring six inches across the lowest floret. Upper blooms are progressively smaller.

*Form.*—Flowers are wide-open, recurved and some petals are rolled back so that the tips come to a point.

Petals:

*Size.*—Three upper petals are 1¾ to 2½ inches in diameter; lower petals 1¼ to 2 inches wide.

*Substance.*—Heavy; surface smooth with some petals creased at the center toward the tips.

*Fragrance.*—None.

*Color.*—The color in the British Horticultural Colour Chart which most closely resembles my variety is Brick Red (016). The color shades from 016/3 in the upper throat to 016 in the blotch on the lower petal or petals. A faint Primrose Yellow (601/3) line runs through the blotches on the lower petals.

Reproductive organs:

*Stamens.*—Slightly deeper than the deepest shade of the flower.

*Pistils.*—Nearly white. They extend about the same distance as the stamens.

*Comparisons*

My new variety resembles Dusty Miller (unpatented) more than any other known variety but differs from it principally as follows:

(1) My variety is larger and taller than Dusty Miller.

(2) My variety has a novel contrasting blotch and Dusty Miller is nearly a self color.

(3) My variety has a more distinctive form than Dusty Miller.

(4) My variety is healthier and makes larger and redder bulbs than Dusty Miller.

(5) My variety has more buds than Dusty Miller.

(6) My variety has more of a brown tone than Dusty Miller.

Having thus disclosed my invention, I claim:

The new variety of gladiolus plant substantially as herein described and illustrated, characterized by its large size, the general symmetry and regular placement of its flowers, the unusually smooth and colorful bulbs and the novel and beautiful combination of colors of the flowers.

No references cited.